(12) United States Patent
Woltman et al.

(10) Patent No.: US 8,793,163 B2
(45) Date of Patent: Jul. 29, 2014

(54) PACKAGE AND METHOD FOR CREATING SUCH A PACKAGE FOR ASSISTING A PERSON IN TRANSITIONING FROM ONE DISPOSABLE ABSORBENT PRODUCT TO ANOTHER

(71) Applicant: Kimberly-Clark Worldwide, Inc., Neenah, WI (US)

(72) Inventors: Garry Roland Woltman, Appleton, WI (US); Christoph Zickler, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/974,557

(22) Filed: Aug. 23, 2013

(65) Prior Publication Data
US 2013/0346238 A1    Dec. 26, 2013

Related U.S. Application Data

(60) Division of application No. 13/751,632, filed on Jan. 28, 2013, now Pat. No. 8,548,875, which is a continuation of application No. 12/762,884, filed on Apr. 19, 2010, now Pat. No. 8,386,326, which is a division of application No. 11/304,342, filed on Dec. 15, 2005, now abandoned.

(51) Int. Cl.
*G06Q 30/00* (2012.01)

(52) U.S. Cl.
USPC .................................................. 705/26.1

(58) Field of Classification Search
CPC ......................................... G06Q 30/06–30/08
USPC ............................................... 705/26.1–27.2
See application file for complete search history.

(56) References Cited

U.S. PATENT DOCUMENTS

| 5,797,755 A | 8/1998 | Montgomery |
| 5,821,872 A | 10/1998 | Brown et al. |

(Continued)

FOREIGN PATENT DOCUMENTS

| EP | 0765506 B1 | 1/1999 |
| EP | 0986996 A2 | 3/2000 |

(Continued)

OTHER PUBLICATIONS

"The Selling of Incontinence," Consumer Reports, Oct. 1997, pp. 65-67.

(Continued)

*Primary Examiner* — Ethan D Civan
(74) *Attorney, Agent, or Firm* — Armstrong Teasdale LLP

(57) ABSTRACT

A package includes a plurality of a first absorbent product from a first product category and at least one sample of a second absorbent product from a second product category. The first absorbent product and the second absorbent product have a common characteristic. A transition aid has a first region including a depiction of the first absorbent product, a second region including a depiction of the second absorbent product, and a third region including at least one scale of reference comprising a depiction of the common characteristic of both the first absorbent product and the second absorbent product. The depiction of each of the first absorbent product and the second absorbent product is positioned along the scale to indicate the common characteristics of each product. A method for creating such a package is also disclosed.

18 Claims, 8 Drawing Sheets

(56) References Cited

U.S. PATENT DOCUMENTS

| | | |
|---|---|---|
| 5,839,585 A | 11/1998 | Miller |
| 5,865,322 A | 2/1999 | Miller |
| 5,947,302 A * | 9/1999 | Miller .................. 211/49.1 |
| 6,093,027 A | 7/2000 | Unger et al. |
| 6,250,929 B1 | 6/2001 | Kolb et al. |
| 6,284,942 B1 | 9/2001 | Rabin |
| 6,304,854 B1 | 10/2001 | Harris |
| 6,375,077 B1 | 4/2002 | Hankins |
| 6,454,095 B1 | 9/2002 | Brisebois et al. |
| 6,601,705 B2 | 8/2003 | Molina et al. |
| 6,604,609 B2 | 8/2003 | Bruce et al. |
| 6,612,846 B1 | 9/2003 | Underhill et al. |
| 6,648,864 B2 | 11/2003 | Ronn et al. |
| 6,679,705 B2 | 1/2004 | Supinski et al. |
| 6,685,020 B2 | 2/2004 | Briseboi et al. |
| 6,763,944 B2 | 7/2004 | Ronn et al. |
| 6,884,238 B2 | 4/2005 | Underhill et al. |
| 6,890,182 B2 | 5/2005 | Healey et al. |
| 6,896,521 B2 | 5/2005 | Underhill et al. |
| 6,923,321 B2 | 8/2005 | Samolinski et al. |
| 7,549,538 B2 | 6/2009 | Naoe et al. |
| 2001/0051953 A1 | 12/2001 | Fukuma et al. |
| 2002/0046132 A1 | 4/2002 | Raye et al. |
| 2002/0066688 A1 | 6/2002 | Autterson |
| 2002/0095329 A1 | 7/2002 | Malik et al. |
| 2003/0033219 A1 | 2/2003 | Kasahara et al. |
| 2003/0061202 A1 | 3/2003 | Coleman |
| 2003/0102238 A1 | 6/2003 | White et al. |
| 2003/0103070 A1 | 6/2003 | Tiongson et al. |
| 2003/0112272 A1 | 6/2003 | Gantenhammer |
| 2003/0127351 A1 | 7/2003 | Takahashi et al. |
| 2003/0234199 A1 | 12/2003 | Morita et al. |
| 2004/0122744 A1 | 6/2004 | Heki et al. |
| 2004/0122745 A1 | 6/2004 | Hantke et al. |
| 2005/0065492 A1 * | 3/2005 | Cole et al. ................ 604/385.01 |
| 2005/0197893 A1 | 9/2005 | Landau et al. |

FOREIGN PATENT DOCUMENTS

| | | |
|---|---|---|
| EP | 1117055 A2 | 7/2001 |
| EP | 1197897 A1 | 4/2002 |
| EP | 1306069 A2 | 5/2003 |
| GB | 2386235 A | 9/2003 |
| JP | 2001356715 A | 12/2001 |
| JP | 2002304555 A | 10/2002 |
| JP | 2003260031 A | 9/2003 |
| WO | 0013632 A1 | 3/2000 |
| WO | 0039702 A2 | 7/2000 |
| WO | 0111532 A1 | 2/2001 |
| WO | 0175729 A2 | 10/2001 |
| WO | 0195845 A1 | 12/2001 |
| WO | 0203902 A2 | 1/2002 |
| WO | 0230347 A1 | 4/2002 |
| WO | 0233628 A2 | 4/2002 |
| WO | 0234127 A1 | 5/2002 |
| WO | 02096331 A2 | 12/2002 |
| WO | 03036421 A2 | 5/2003 |
| WO | 03050011 A1 | 6/2003 |
| WO | 2004026203 A2 | 4/2004 |
| WO | 2005061338 A1 | 7/2005 |

OTHER PUBLICATIONS

"Tampons and Pads: Should You Use What Mom Used?," Consumer Reports, Jan. 1995, pp. 51-55.

"Disposable Diapers: Time to Change Brands?," Consumer Reports, Mar. 2004, pp. 34-35.

* cited by examiner

PACKAGE AND METHOD FOR CREATING SUCH A PACKAGE FOR ASSISTING A PERSON IN TRANSITIONING FROM ONE DISPOSABLE ABSORBENT PRODUCT TO ANOTHER

CROSS REFERENCE TO RELATED APPLICATIONS

This application is a divisional application of U.S. patent application Ser. No. 13/751,632 filed Jan. 28, 2013, which a continuation application of U.S. patent application Ser. No. 12/762,884 filed Apr. 19, 2010, now U.S. Pat. No. 8,386,326, which is a divisional application of U.S. patent application Ser. No. 11/304,342 filed Dec. 15, 2005, now abandoned. Each of these applications are incorporated herein by reference it their entireties.

BACKGROUND

The present disclosure generally relates to methods for assisting consumers in transitioning from a current absorbent product to a future absorbent product. Also described are aids for assisting in this transition. In particular, the transition aids provide a consumer with a means for comparing different characteristics of their current absorbent product with characteristics of a future absorbent product.

Absorbent articles function both to contain discharged body materials and to isolate these materials from the body of the wearer and from the wearer's garments and bed clothing. Disposable absorbent articles having many different basic designs are known in the art. For example, feminine hygiene products such as sanitary napkins and panty liners are absorbent articles that are typically worn in the crotch region of an undergarment. Interlabial absorbent articles are feminine hygiene products that are typically designed to be worn within the interlabial space of a wearer. Other feminine hygiene absorbent articles such as tampons are designed to be worn within the vaginal interior. Adult incontinence products such as incontinent pads, shields, guards, undergarments, briefs, and the like, and children's diapers and training pants are typically worn in the crotch region of an undergarment or worn as an undergarment. All of these absorbent articles are designed to absorb or otherwise contain liquid and other discharges from the human body and to prevent body and clothing soiling.

The number of different types and features of absorbent products often makes it confusing to consumers which products would best meet their protection needs. For example, absorbent products may vary in their absorbent capacities, their size (e.g., their length, the area of undergarment which they cover, etc.), their thicknesses, and their inclusion or non-inclusion of certain features such as wings, flaps, and the like. In addition, even if a consumer has selected a product that meets his or her needs, the product may not be available at the store at which the consumer is currently shopping. As such, the consumer may be forced to make an alternative selection of a less appropriate product.

While the manufacturers of such products have been adept at providing an adequate selection of absorbent products having different features and degrees of protection, they have had less success in educating the individual consumer as to which product is appropriate for the individual consumer's needs. Even when consumers have been successfully educated as to the best product for their protection needs, not all stores may stock the best product, but rather may only stock some closely related products. Currently, consumers in these situations are left to a "trial and error" approach to selecting an appropriate absorbent article from those available. They must buy a product having a particular feature, try the product to determine if the product is appropriate for their protection needs, and then reselect another product having a different feature, if the previously selected product is found to be inadequate for their needs. For example, if a consumer is interested in a product having a particular absorbency, the consumer must buy a product having a particular absorbency level, try the product to determine if either leakage occurs or under utilized capacity is present, and then reselect another absorbency level having either a higher or lower absorbency depending on the previous results, until the appropriate product for their needs is found. Such a process can be aggravating to the consuming at best, or worse, it could traumatize the consumer if they used an inappropriate product that leaked in public. Either situation can alienate the consumer from ever using that brand or type of absorbent article again.

This issue is particularly problematic when a consumer is transitioning from one type or brand of absorbent article to another. Consumers typically do not have a good understanding about how their current absorbent product compares to other available products on the market. For example, if a consumer is transitioning from a feminine hygiene product, such as a napkin or pad, to an incontinence product, it may be difficult for the consumer to determine how the features of her current napkin or pad compare to the features of the needed incontinence product. The same may be true for consumers transitioning from a product provided by one company to a similar product provided by another company.

Therefore, there is a need for a method for assisting a consumer in transitioning from a currently used absorbent product to a future absorbent product, and for recommending an appropriate future absorbent product. In addition, there is a need for instructional material designed to aid consumers in transitioning from their current absorbent product to a future absorbent product.

SUMMARY

The present disclosure generally relates to methods for assisting consumers in transitioning from a current absorbent product to a future absorbent product. Also described are transition aids for assisting in this transition. In particular, the transition aids provide a consumer with a means for comparing different characteristics of their current absorbent product with characteristics of a future absorbent product.

In one embodiment, the present disclosure provides a transition aid for assisting a consumer in transitioning from a current absorbent product choice to a future absorbent product choice. The transition aid comprises a first region comprising a depiction of a first group of related absorbent products, wherein the first group of related absorbent products comprises a current absorbent product choice of the consumer; a second region comprising a depiction of a second group of related absorbent products, wherein the second group of related absorbent products comprises a future absorbent product choice of the consumer; and a third region comprising at least one scale of reference comprising a depiction of a common characteristic of both the first group of related absorbent products and of the second group of related absorbent products; wherein the depiction of each of the first and second group of related absorbent products is positioned along the scale to indicate the common characteristic of each depicted product.

Also provided is a transition aid for assisting a consumer in transitioning from a current absorbent product choice to a future absorbent product choice. The transition aid comprises a first region comprising a depiction of a first group of related absorbent products wherein the first group of related absorbent products comprises a current absorbent product choice of the consumer; a second region comprising a depiction of a second group of related absorbent products, wherein the second group of related absorbent products comprises a future absorbent product choice of the consumer; a third region comprising a scale of reference comprising a depiction of a first common characteristic of both the first group of related absorbent products and of the second group of related absorbent products; wherein the third region is adjacent to both the first region and the second region and wherein the depiction of each of the products in the first region and in the second region is positioned along the scale of the third region to indicate the common characteristic of each depicted product; a fourth region comprising a depiction of the first group of related absorbent products; a fifth region comprising a depiction of the second group of related absorbent products; and a sixth region comprising a scale of reference comprising a depiction of a second common characteristic of both the first group of related products and of the second group of related products; wherein the sixth region is adjacent to both the fourth region and the fifth region and wherein the depiction of each of the products in the fourth region and in the fifth region is positioned along the scale of the sixth region to indicate the common characteristic of each depicted product.

In another embodiment, the present disclosure provides a transition aid for assisting a consumer in transitioning from a current absorbent product choice to a future absorbent product choice. The transition aid comprises a first region comprising a depiction of a group of related absorbent products; a second region comprising a scale of reference comprising a depiction of a first common characteristic of the group of related absorbent products; wherein the second region is adjacent to the first region and wherein the depiction of each of the products in the first region is positioned along the scale of the second region to indicate the common characteristic of each depicted product; a third region comprising a depiction of the group of related absorbent products; and a fourth region comprising a scale of reference comprising a depiction of a second common characteristic of the group of related absorbent products; wherein the fourth region is adjacent to the third region and wherein the depiction of each of the products in the third region is positioned along the scale of the fourth region to indicate the common characteristic of each depicted product.

Also provided is a method for assisting a consumer in transitioning from a current absorbent product choice to a future absorbent product choice. The method comprises receiving personal information from the consumer about at least one need of the consumer; receiving information from the consumer about an absorbent product currently used by the consumer; selecting a first group of related absorbent products, wherein the first group of related absorbent products comprise the current absorbent product choice of the consumer; selecting at least one additional group of related absorbent products; and providing the consumer with a transition aid, the transition aid comprising a first region comprising a depiction of the first group of related absorbent products, a second region comprising a depiction of the at least one additional group of related absorbent products, and a third region comprising at least one scale of reference comprising a depiction of a common characteristic of both the first group of related absorbent products and of the at least one additional group of related absorbent products, wherein the depiction of each of the first and at least one additional group of related absorbent products is positioned along the scale to indicate the common characteristic of each depicted product.

Also provided is a method for assisting a consumer in transitioning from a current absorbent product choice to a future absorbent product choice. The method comprises receiving information from a store about the availability of the absorbent products; selecting a first group of related absorbent products, wherein the first group of related absorbent products comprise the current absorbent product choice of the consumer; selecting at least one additional group of related absorbent products, wherein the at least one additional group of related absorbent products are available from the store; and providing the consumer with a transition aid, the transition aid comprising a first region comprising a depiction of the first group of related absorbent products, a second region comprising a depiction of the at least one additional group of related absorbent products, and a third region comprising at least one scale of reference comprising a depiction of a common characteristic of both the first group of related absorbent products and of the at least one additional group of related absorbent products, wherein the depiction of each of the first and at least one additional group of related absorbent products is positioned along the scale to indicate the common characteristic of each depicted product.

In still another embodiment, a method for creating a package comprising a transition aid for transitioning a consumer from an absorbent product in a first product category to an absorbent product in a second product category is provided. The method generally comprises selecting a first absorbent product in the first product category and selecting, by a processor, a second absorbent product in the second product category. The first absorbent product and the second absorbent product have a common characteristic. A package is created for the first absorbent product. The package comprises a plurality of the first absorbent product, at least one sample of the second absorbent product, and a transition aid. The transition aid comprises a first region comprising a depiction of the first absorbent product, a second region comprising a depiction of the second absorbent product, and a third region comprising at least one scale of reference comprising a depiction of the common characteristic of both the first absorbent product and the second absorbent product. The depiction of each of the first absorbent product and the second absorbent product is positioned along the scale to indicate the common characteristics of each of the first absorbent product and the second absorbent product.

In a further embodiment, a system for creating a package comprising a transition aid for transitioning a consumer from an absorbent product in a first product category to an absorbent product in a second product category is provided. The system generally comprises a computing device and a processor programmed to receive, from the consumer, a selection of a first absorbent product in the first product category; select a second absorbent product in the second product category, wherein the first absorbent product and the second absorbent product have a common characteristic; and provide instructions to create a package for the first absorbent product. The package comprises a plurality of the first absorbent product, at least one sample of the second absorbent product and a transition aid. The transition aid comprises a first region comprising a depiction of the first absorbent product, a second region comprising a depiction of the second absorbent product, and a third region comprising at least one scale of reference comprising a depiction of the common characteristic of both the first absorbent product and the second absorbent product. The depiction of each of the first absorbent product and the second absorbent product is positioned along the scale to indicate the common characteristics of each of the first absorbent product and the second absorbent product.

In another embodiment, a package generally comprises a plurality of a first absorbent product from a first product category and a transition aid. The transition aid comprises a first region comprising a depiction of the first absorbent product, a second region comprising a depiction of a second absorbent product from a second product category wherein the first absorbent product and the second absorbent product have a common characteristic, and a third region comprising at least one scale of reference comprising a depiction of the common characteristic of both the first absorbent product and the second absorbent product. The depiction of each of the first absorbent product and the second absorbent product is positioned along the scale to indicate the common characteristics of each of the first absorbent product and the second absorbent product.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1A:
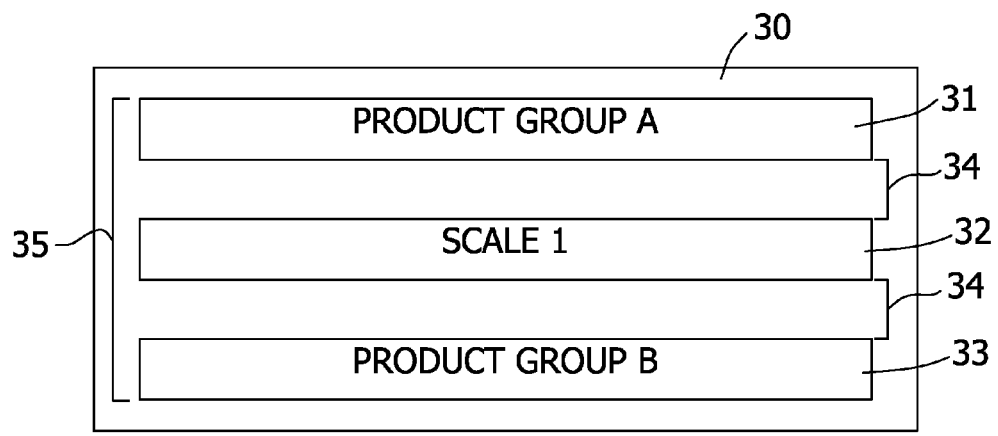
FIGS. 1A and 1B illustrate various configurations of a transition aid of the present disclosure.

The present disclosure generally relates to methods for assisting consumers in transitioning from a current absorbent product to a future absorbent product. Also described are transition aids for assisting in this transition. In particular, the transition aids provide a consumer with a means for comparing different characteristics of their current absorbent product with characteristics of a future absorbent product.

As used herein, the phrase "absorbent article" generally refers to devices which absorb and contain body fluids, and more specifically, refers to devices which are placed against or near the skin to absorb and contain the various fluids discharged from the body. The phrase "absorbent article" may include both disposable and non-disposable absorbent articles. Examples of absorbent articles include absorbent articles intended for personal wear, such as diapers and training pants; incontinence products, such as pads, shields, guards, undergarments, briefs, and the like; feminine hygiene products, such as sanitary napkins, panty liners, tampons, interlabial pads, and the like; other personal garments; bandages; and the like.

The term "disposable" is used herein to describe absorbent articles which are not intended to be laundered or otherwise restored or reused as an absorbent article (i.e., they are intended to be discarded after a single use).

The term "absorbent product" is intended to include an absorbent article, as well as a package comprising a plurality of individual absorbent articles.

The term "consumer" is intended to include both the user of the absorbent article, as well as a caregiver and/or a purchaser of the absorbent product.

The term "store" is intended to include institutions, retailers, or other stores that provide a product to consumers.

The terms "current absorbent product" or "current absorbent product choice" are used herein to describe an absorbent product (or products) that is currently being used or purchased by a consumer.

The terms "future absorbent product" or "future absorbent product choice" are used herein to describe an absorbent product (or products) that is not currently being used or purchased by a consumer but that a consumer may potentially transition into (e.g., a product which may potentially be used or purchased by a consumer at some future time).

In one aspect, the present disclosure provides a transition aid for assisting a consumer in transitioning from one product to another product. Preferably, the product is an absorbent product. In particular, the transition aid provides a means by which a consumer can compare an absorbent product he or she is currently using to other absorbent products on the market. Typically the comparison is between two or more groups of related products. For example, in one embodiment, the transition aid comprises at least three distinct and separate regions. One region may comprise a depiction of a first group of absorbent products that are related to each other in some way, a second region may comprise a depiction of a second group of absorbent products that are related to each other in some way, and a third region may comprise at least one scale of reference that comprises a depiction of a common characteristic of both the first and the second groups of related absorbent products. Typically, the consumer's current absorbent product choice is among the first group of related products, and the consumer's future absorbent product choice is among the second group (and/or third, fourth, fifth, etc. groups, if applicable) of related products. The scale of reference provides a means by which the different groups of related products may be compared.

The transition aids of the present invention may be in any form suitable for conveying information to the consumer. Preferably, the transition aid is a visual aid. Alternately, or in addition, the transition aid may be a tactile aid, i.e., the transition aid is in a form that delivers information to the consumer through touch. For example, the transition aid may comprise varied arrangements of raised markings or dots, such as Braille writing, that can be identified by the consumer by touch. Although discussed primarily in terms of a visual aid, it is to be understood that the transition aids of the present disclosure may be in other suitable forms.

Generally, the absorbent products depicted in each region of the transition aid are related to each other according to at least one common characteristic, i.e., the products within each region share some characteristic or relationship with the other products within the region. The common characteristic may be related to some need or desire of the consumer, and may include, for example, a feature, a benefit, an attribute, a brand, a company, a distribution channel, a manufacturer, a product category, or some combination thereof. For example, in one embodiment, the products may be related according to product category, i.e., all the products in the particular group are from the same product category. As used herein, the term "product category" means a group of products having some features that are the same or a collection of products sharing a common attribute. A product category may be general, or more specific. A general product category may include, for example, feminine hygiene products generally, incontinence products generally, children's diapers generally, training pants generally, and the like. A product category may also be more specific. For example, a product category may be a particular type of absorbent article, such as tampons, interlabial pads, sanitary napkins, panty liners, incontinence pads, incontinence shields, incontinence guards, incontinence undergarments, or incontinence briefs, or may be a particular type of diaper or training pant, and the like.

It is advantageous to group the products according to product category in situations where the consumer is transitioning from one product category to another. For example, a consumer may be transitioning from a feminine hygiene product to an incontinence product, from a diaper to a training pant, or other such transitions. The transition may even be within a general product category, e.g., from a tampon or interlabial pad to a sanitary napkin or panty liner. In these situations, one region of the transition aid typically comprises a depiction of a first group of related products from one product category, and a different region of the transition aid may comprise a depiction of a second group of products that are related according to a different product category. Typically, the consumer's current product choice will be among either the first or second group, and the consumer's future product choice will be among the other group or groups.

In another embodiment, the products may be related according to availability. For example, the group of products depicted in one region of the transition aid may be available from one or more manufacturers or stores, and the group of products depicted in a different region of the transition aid may be products available from a different manufacturer or store.

In another embodiment, the products may be related according to brand and/or company. For example, the group of products depicted in one region of the transition aid may be of one brand and/or be made by one company, and the group of products depicted in a different region of the transition aid may be of a different brand and/or be made by a different company. This type of grouping is particularly beneficial for consumers who may wish to try a product similar to their current product, but that is made by a different company, or for consumers who may wish to try a product of a different brand.

In still another embodiment, the products may be related according to features, benefits, and/or attributes of the products. As used herein, the term "benefits" means a product attribute that is expressed in terms of what the consumer gets from the product, rather than its physical characteristics or features. Examples of benefits include protection, comfort discretion, convenience, price, and the like. As used herein, the term "attributes" means product features, functionality, and performance of the absorbent products that are designed into the product. Examples of product attributes include absorbency, saturation retention capacity, rewet capacity, dryness, and the like. As used herein, the term "features" means the solution to a consumer need or problem, i.e., the way the benefits are provided to the consumer. Examples of product features include type of cover materials (e.g., film, nonwoven, etc.), wings/non-wings, product elements designed for odor control, thickness, length of the product, flat or curved product, and the like. This type of grouping is particularly beneficial when a consumer is interested in an absorbent product having a certain benefit, feature, and/or attribute, or a particular mixture of benefits, features, and/or attributes.

The products in one group of products may be related to each other according to the same characteristic by which another group of products are related, or alternately, may be related according to a different characteristic(s). For example, in one embodiment, a first group of related products in one region may be related to each other according to product category, and a second (or additional) group of related products in a different region may also be related to each other according to product category. Typically, in this instance, the absorbent products in the first group of related products are of one product category (e.g., feminine hygiene products) and the absorbent products in the second (or additional) group of related products are of a different product category (e.g., incontinence products). Alternately, in another example, a first group of related products may be related to each other according to product category, and a second (or additional) group of related products may be related to each other according to a different characteristic (e.g., a different feature, benefit, attribute, etc.). Numerous combinations of other product characteristics may likewise be compared using a transition aid of the present invention.

Figure 2:
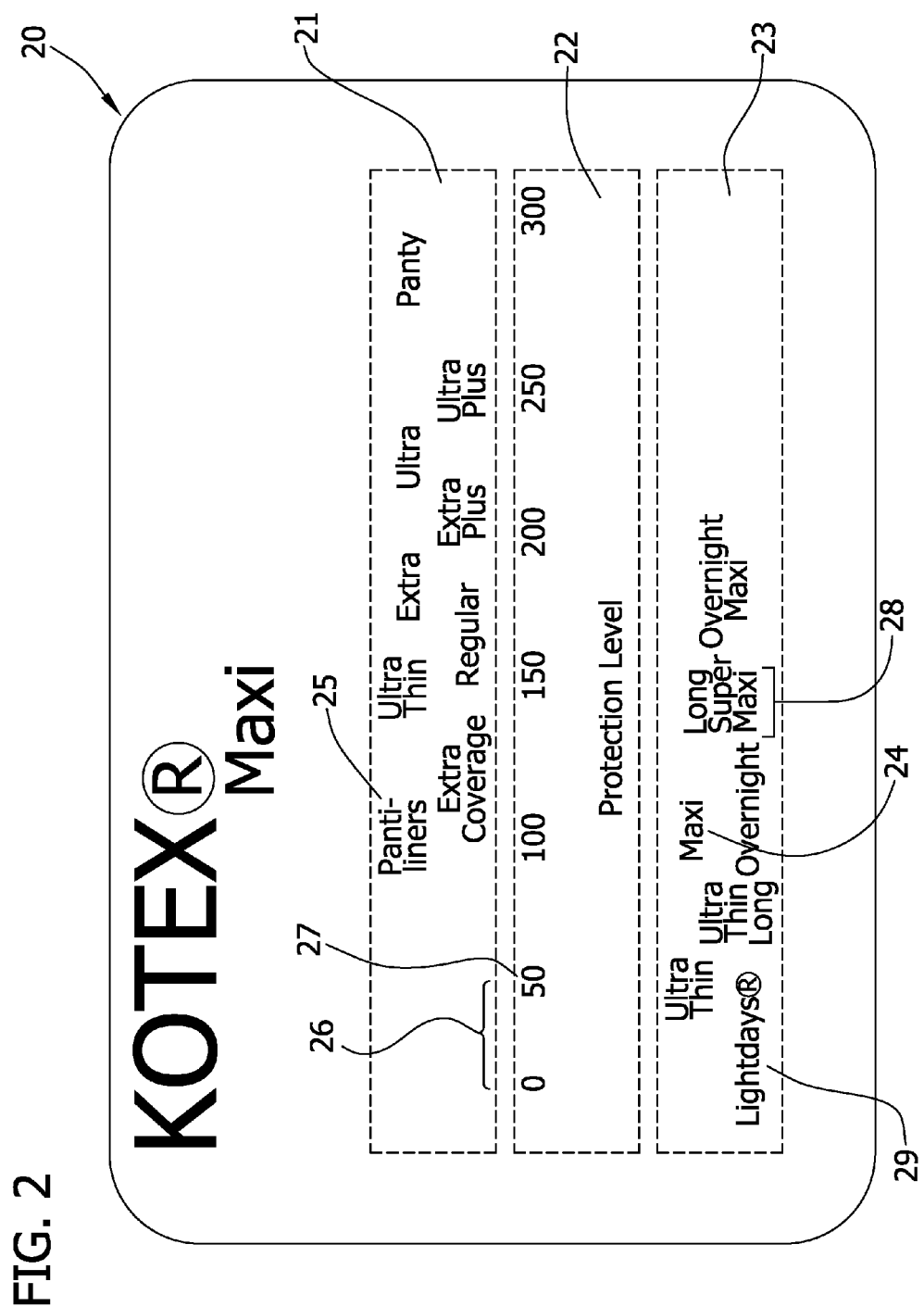
FIG. 2 is a depiction of a transition aid of the present disclosure.

The groups of related absorbent products may be depicted on the transition aid using any suitable method. For example, the absorbent products may be depicted using a letter, a number, a word, a symbol, a picture, or combinations thereof. In one example, one or all of the groups of related products are depicted as a collection of words, with each individual absorbent product in the group being identified by a particular word (or words). An example of this embodiment is illustrated in FIG. 2, wherein the name of each individual absorbent product in the depicted groups are identified by a particular word 29 or words 28. In certain embodiments, the word or image depicting the consumer's current product choice may be highlighted or otherwise emphasized in the collection of words or images for easier identification. In instances where the transition aid provides a recommendation of a future product choice, as discussed below, the depiction of the recommended future product choice may likewise be highlighted or emphasized.

As discussed above, the transition aid may also comprise at least one scale of reference. The scale of reference typically comprises a depiction of a common characteristic of the groups of related absorbent products depicted in other regions of the transition aid, and provides a means by which the comparison of groups of related absorbent products may be made. The common characteristic depicted in the scale of reference may be related to a consumer need or desire, and may include, for example, a benefit, an attribute, a feature, and combinations thereof, as discussed above. Typically, the scale of reference depicts a range of values of a certain common characteristic shared by one or more groups of related products depicted in other regions of the transition aid. For example, in one embodiment, the scale of reference may depict a range of values for absorbent capacity. Typically, the values are ordered marks arranged on the scale at a fixed interval. The values may be depicted using any suitable means including, for example, a letter, a number, a word, a symbol, a picture, or combinations thereof.

The transition aids of the present invention may comprise one scale of reference, or alternately, may comprise two or more scales of reference. Using two or more scales of reference is advantageous if multiple comparisons are to be made between the related groups of absorbent products. Although each scale typically depicts a different product characteristic, it is also contemplated that a visual aid may comprise two or more scales, with each scale depicting the same product characteristic.

In certain instances where the transition aids comprise more than one scale of reference, the scales of reference may be located together in one region of the transition aid, or more preferably, each scale may be located in a distinct region of the transition aid.

The various regions of the transition aid are typically arranged so that each region is adjacent to at least one other region of the transition aid. For purposes of the present disclosure, two regions are "adjacent" to each other if they are not separated by a third region. There may, however, optionally be some spacing between some or all of the regions of the transition aid, and even between two adjacent regions (e.g., two regions may be adjacent to each other even if they are not directly contacting each other). For example, referring to FIG. 1A, the region 31 comprising Product Group A is adjacent to the region 32 comprising Scale 1, even though the region 31 comprising Product Group A and the region 32 comprising Scale 1 are not in direct contact, i.e., they are separated by a space 34.

Typically, the region (or regions) comprising the scale is located between the region comprising the current product choice and the region comprising the future product choice to allow for easy comparison. However, other configurations are also possible. For example, the region comprising the scale of reference may be adjacent to only one other region, e.g., adjacent to the region comprising the consumer's current product choice or adjacent to the region comprising the consumer's future product choice. In instances where the transition aid comprises more than one region comprising a scale of reference, other configurations are also possible.

Figure 1B:
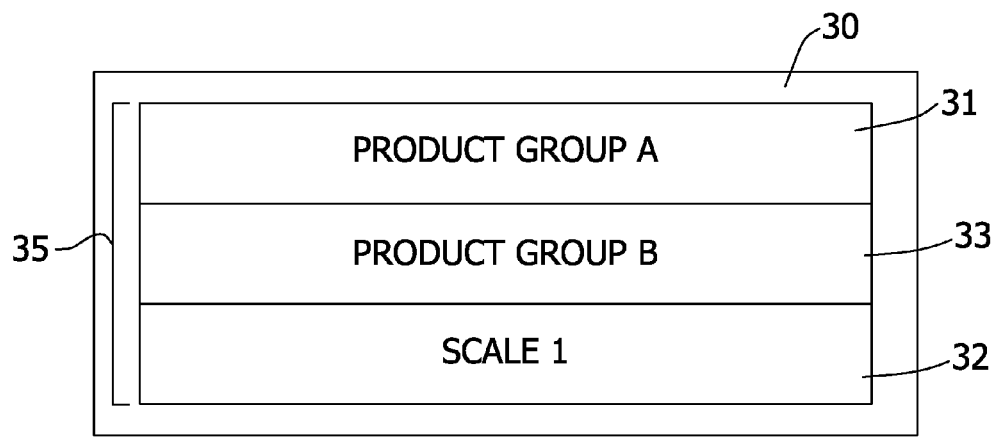

Referring to FIG. 1A, one configuration of a visual aid of the present disclosure is illustrated. The visual aid 35 comprises three different regions. One region 31 comprises a depiction of a first group of related products (e.g., Product Group A), a second region 33 comprises a depiction of a different group of related products (e.g., Product Group B), and a third region 32 comprises a scale of reference (e.g., Scale 1). As discussed herein, the scale of reference may comprise a depiction of a common characteristic of both groups of related products (e.g., a characteristic of Product Group A and Product Group B). The three regions are depicted on a medium 30, and optionally a space 34 separates two or more of the regions. As can be seen from FIG. 1A, the region 32 comprising the scale of reference may be positioned so that it is adjacent to both regions 31, 33 depicting the two groups of products that are being compared. Alternately, as illustrated in FIG. 1B, the region 32 comprising the scale of reference may be positioned so that it is adjacent to only one of the other regions.

Typically, the products depicted in each region of the visual aid are positioned within the region so that they line up in some manner with corresponding markings on the scale of reference. For example, referring now to FIG. 2, an exemplary visual aid present on a package of absorbent products 20, is depicted. A first region 23 of the visual aid comprises a depiction of a group of products related according to one product category, e.g., feminine hygiene products. A second region 21 comprises a depiction of a group of products related according to a different product category, e.g., incontinence products. A third region 22 of the visual aid comprises a scale of reference that depicts a common characteristic of the absorbent products depicted in the first region 23 and the second region 21. The scale of reference depicts a range of values for a particular product characteristic, in this example absorbent capacity in grams, that is represented on the scale as ordered marks 27 at a fixed interval 26. As can be seen from FIG. 2, the absorbent products depicted in the first region 23 and the second region 21 are positioned within their respective regions so that the individual products line up with the value on the scale that represents the product's particular absorbent capacity. In this manner, a consumer may easily compare how the absorbency of a product in one product category compares to the absorbency of a product in another product category; e.g., how the absorbent capacity of a particular feminine hygiene product compares to the absorbent capacity of a particular incontinence product. For example, a consumer may locate her current product choice 24 in the first region 23 of the visual aid and, referring to the scale of reference in the third region 22, may locate a possible future product choice 25 in the second region 21 that has a similar absorbent capacity as her current product choice 24.

A similarly arranged visual aid may be used to compare other absorbent product characteristics. For example, in another embodiment, the third region 22 may comprise a scale of reference that depicts a different common characteristic (e.g., a different benefit, attribute, and/or feature) of the absorbent products depicted in the first region 23 and the second region 21. In yet a different embodiment, the first region 23 and the second region 21 may comprise depictions of groups of products related according to other characteristics. For example, the first region 23 may comprise a depiction of a group of products of one brand and/or that are made by one company, and the second region 21 may comprise a depiction of a group of products of a different brand and/or that are made by a different company.

In certain embodiments, the visual aid may comprise more than two regions each depicting a different group of related products and one or more region comprising one or more scale of reference. For example, referring to FIG. 3A, another configuration of a visual aid of the present invention is illustrated. The visual aid 47 comprises four different regions located on a medium 40 that are optionally separated by a space 44 between regions. A first region 41 comprises a depiction of a first group of related products (e.g., Product Group A), a second region 43 comprises a depiction of a second group of related products (e.g., Product Group B), a third region 45 comprises a depiction of a third group of related products (e.g., Product Group C), and a fourth region 42 comprises a scale of reference (e.g., Scale 1). As discussed above, the scale of reference typically comprises a depiction of a common characteristic of the groups of related products that are being compared. In this instance, Scale 1 may comprise a depiction of a common characteristic of Product Group A, Product Group B, and Product Group C, to allow for comparison between all three groups of products. As can be seen from FIG. 3A, the region 42 comprising the scale of reference may be positioned so that it is adjacent to two regions depicting two different groups of products that are being compared (e.g., Product Group A and Product Group B). Alternately, as illustrated in FIG. 3B, the region comprising the scale of reference may be positioned so that it is adjacent to only one of the other regions.

Figure 3A:
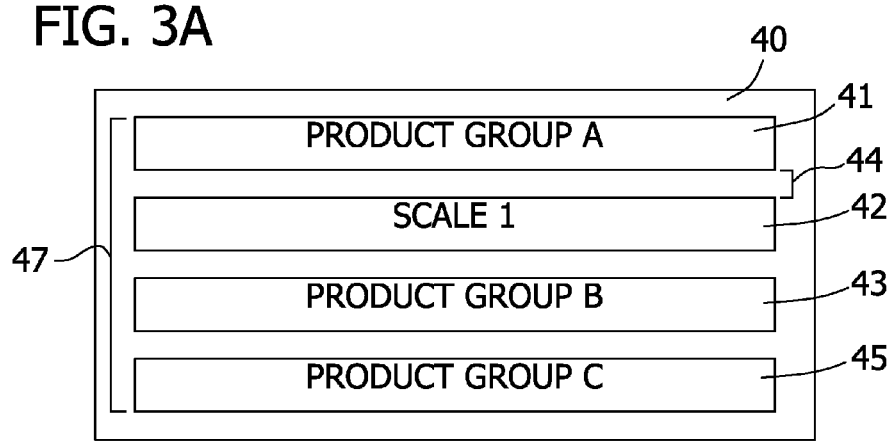
FIGS. 3A, 3B, and 3C illustrate various configurations of a transition aid of the present disclosure.
Figure 3B:
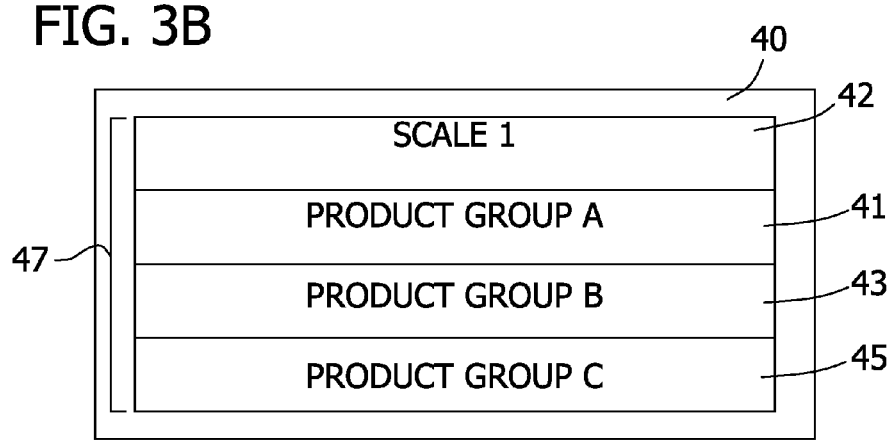
Figure 3C:
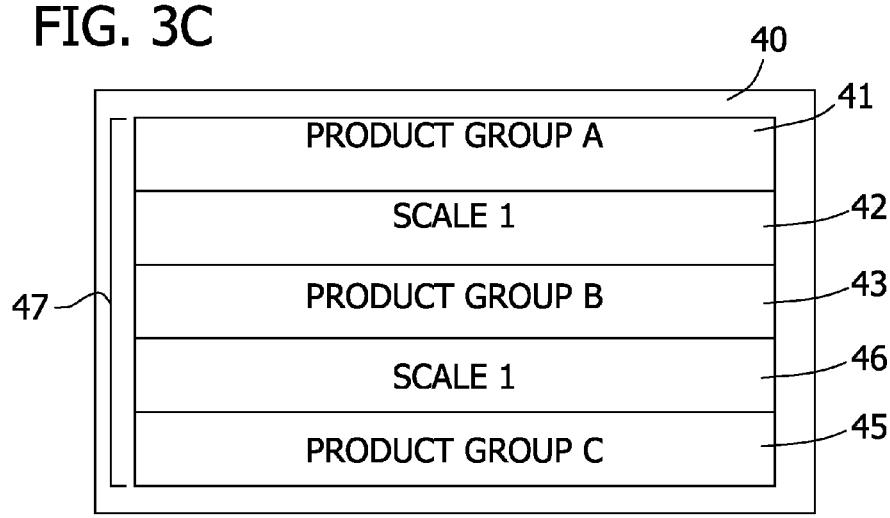

Although the visual aids illustrated in FIGS. 3A and 3B comprise only three different regions that depict groups of related products, it is contemplated that the visual aid may further comprise four, five, or more additional regions that each depict a different group of related products. In instances where the visual aid comprises numerous different regions each depicting a different group of related products, it may be advantageous for the visual aid to comprise two or more regions each comprising the same scale of reference. For example, as illustrated in FIG. 3C, the visual aid may comprise two regions 42, 46 that each comprise the same scale of reference (e.g., Scale 1). The regions comprising the scale of reference are preferably positioned adjacent to different regions depicting the groups of related products, in order to allow for easier comparison of the products using the scale of reference.

Visual aids such as those illustrated in FIGS. 3A, 3B, and 3C are particularly useful for comparing groups of products that are related within each group according to a common characteristic such as product category, company, and/or brand. For example, Product Group A (depicted in a first region 41) may comprise products made by one company, Product Group B (depicted in a second region 43) may comprise products made by a different company, Product Group C (depicted in a third region 45) may comprise products made by yet a different company, and optionally other groups of related products depicted in additional regions (not shown) may comprise products made by still different companies. Scale 1 (depicted in a different region 42) may comprise a depiction of a common characteristic (e.g., a feature, a benefit, an attribute) of Product Group A, Product Group B, Product Group C, and any optional additional groups of related products. In this instance, the products depicted in the first region 41, the second region 43, the third region 45, and any optional additional regions (not shown) are positioned within their respective regions so that the individual products line up with the value on Scale 1 that represents the product's particular characteristic (e.g., absorbent capacity or other such feature, attribute, or benefit). In this manner, a consumer may easily determine how a product made by one company compares to a product made by two or more different companies (e.g., how the absorbent capacity of a group of products made by one company compares to the absorbent capacity of groups of products made by two or more different companies).

Figure 4A:
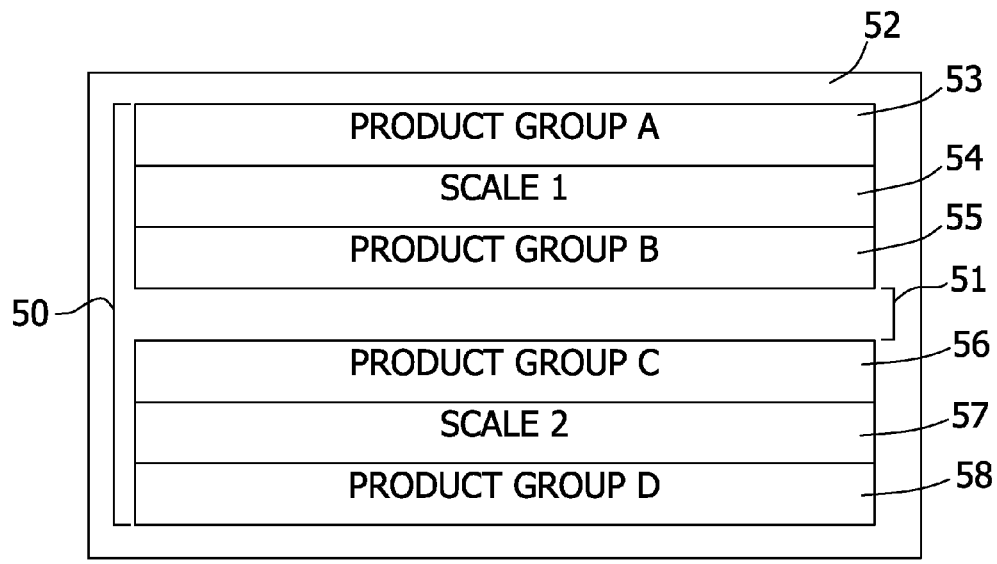
FIGS. 4A, 4B, 4C, and 4D illustrate various configurations of a transition aid of the present disclosure.

Referring to FIG. 4A, another configuration of a visual aid of the present disclosure is illustrated. The visual aid 50 comprises at least six different regions located on a medium 52. The regions are optionally separated by a space 51 between two or more of the regions. A first region 53 comprises a depiction of a first group of related products (e.g., Product Group A), a second region 55 comprises a depiction of a second group of related products (e.g., Product Group B), a third region 54 comprises a first scale of reference (e.g., Scale 1), a fourth region 56 comprises a depiction of a third group of related products (e.g., Product Group C), a fifth region 58 comprises a depiction of a fourth group of related products (e.g., Product Group D), and a sixth region 57 comprises a second scale of reference (e.g., Scale 2). As discussed above, the scale of reference typically comprises a depiction of a common characteristic of the groups of related products that the scale is being used to compare. The visual aid 50 illustrated in FIG. 4A comprises two different scales of reference (e.g., Scale 1 and Scale 2). In this example, Scale 1 may comprise a depiction of a common characteristic of the groups of products it is being used to compare, in this instance a common characteristic of Product Group A and Product Group B, and Scale 2 may comprise a depiction of a common characteristic of the groups of products that it is being used to compare, in this instance a common characteristic of Product Group C and Product Group D.

Figure 4B:
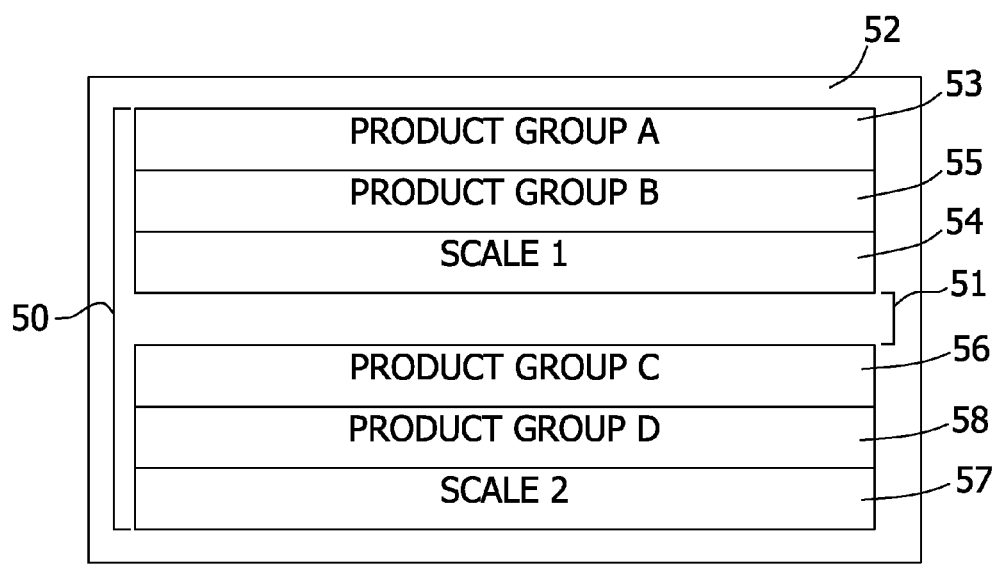
Figure 4C:
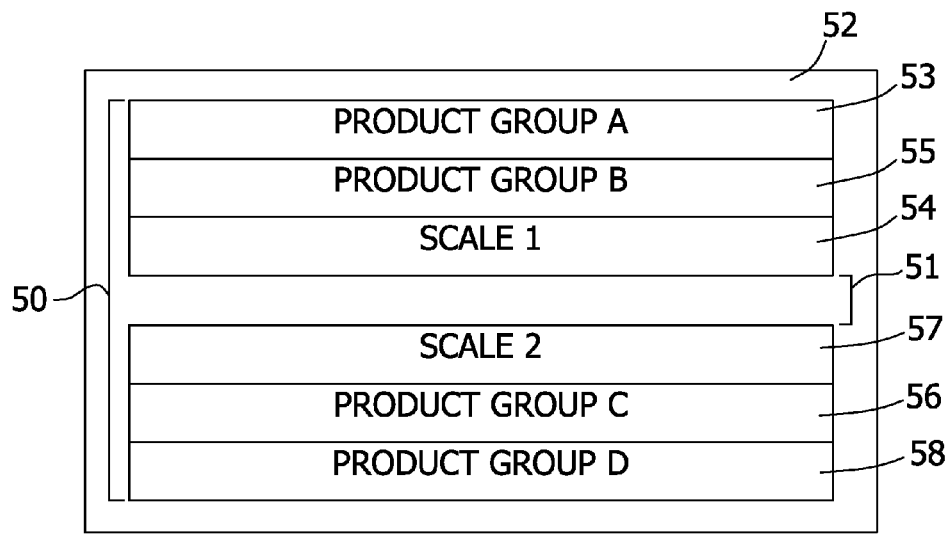
Figure 4D:
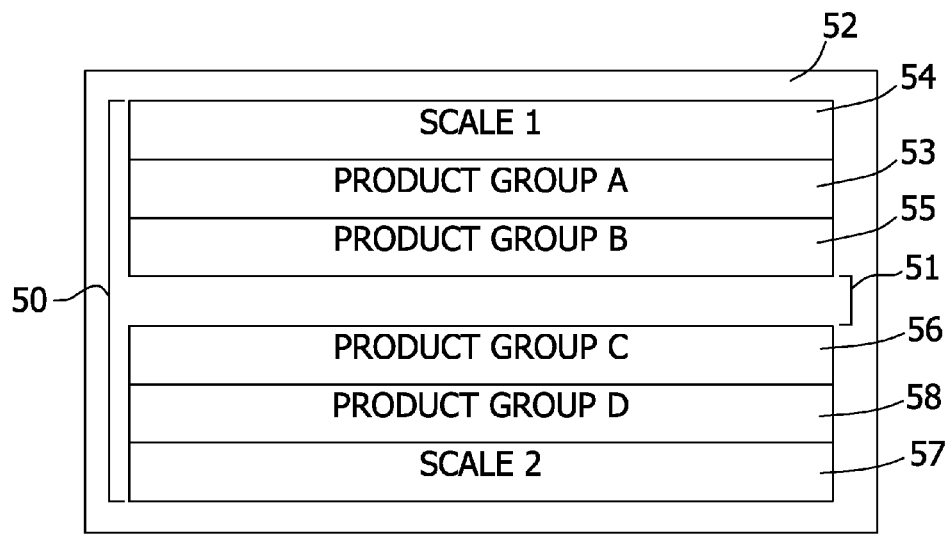

Typically, the scale of reference and the groups of products the scale is being used to compare are grouped together in the visual aid in some manner, to allow for easier comparison. For example, as can be seen from FIG. 4A, the region 54 comprising Scale 1 may be positioned so that it is adjacent to the two regions 53, 55 depicting the groups of products that Scale 1 is being used to compare (e.g., Product Group A and Product Group B). Alternately, as illustrated in FIGS. 4B, 4C, and 4D, the region 54 comprising Scale 1 may be positioned so that it is adjacent to only one of the first region 53 or the second region 55. A similar positioning may be used for the region 57 comprising Scale 2 and the two regions 56, 58 depicting the groups of products that Scale 2 is being used to compare (e.g., Product Group C and Product Group D). Like discussed above, the products depicted in the first region 53 and the second region 55 are positioned within their respective regions so that the individual products line up with the value on the scale in the third region 54 that represents the product's particular characteristic (e.g., some feature, attribute, or benefit of the product), and the products depicted in the fourth region 56 and the fifth region 58 are positioned within their respective regions so that the individual products line up with the value on the scale in the sixth region 57 that represents the product's particular characteristic.

Figure 5A:
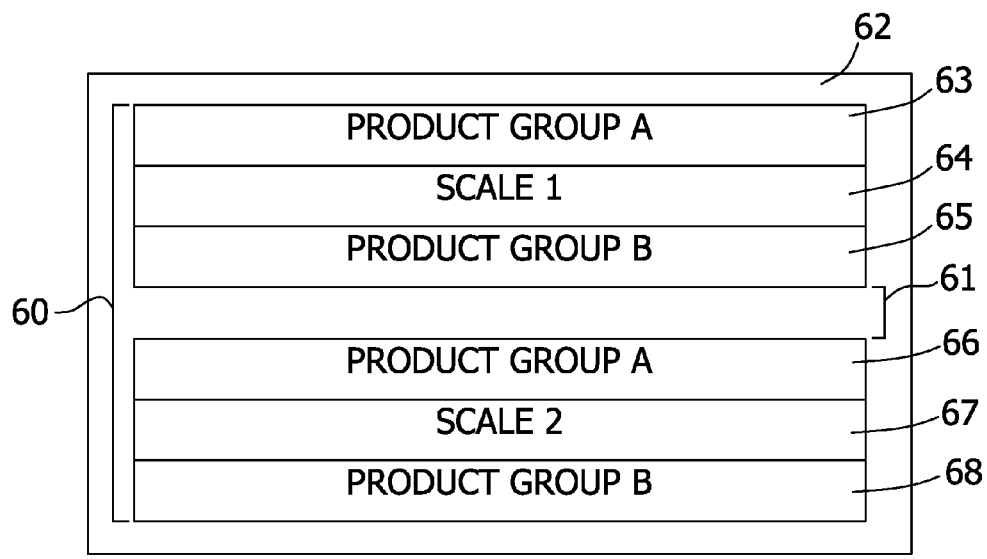
FIGS. 5A, 5B, 5C, and 5D illustrate various configurations of a transition aid of the present disclosure.

In another embodiment, the visual aid may be used to compare two or more groups of related products using two or more different scales of reference. For example, a first group of related products may be compared to a second group of related products (and optionally to a third, fourth, or other additional group of related products) using two or more scales of reference. One example of this embodiment is illustrated in FIG. 5A. In FIG. 5A, the visual aid 60 comprises six different regions located on a medium 62. Two or more of the regions are optionally separated by a space 61 between regions. A first region 63 comprises a depiction of a first group of related products (e.g., Product Group A), a second region 65 comprises a depiction of a second group of related products (e.g., Product Group B), a third region 64 comprises a first scale of reference (e.g., Scale 1), a fourth region 66 comprises another depiction of the first group of related products (e.g., Product Group A), a fifth region 68 comprises another depiction of the second group of related products (e.g., Product Group B), and a sixth region 67 comprises a second scale of reference (e.g., Scale 2). Scale 1 and Scale 2 may each comprise a depiction of a different common characteristic the products in Product Group A and Product Group B. By providing two different scales of reference, the visual aid allows the same two groups of related products to be compared according to more than one characteristic. For example, Scale 1 may be used to compare Product Group A and Product Group B according to price, and Scale 2 may be used to compare Product Group A and Product Group B according to a different characteristic, e.g., absorbency or another such attribute, feature, or benefit.

Figure 5B:
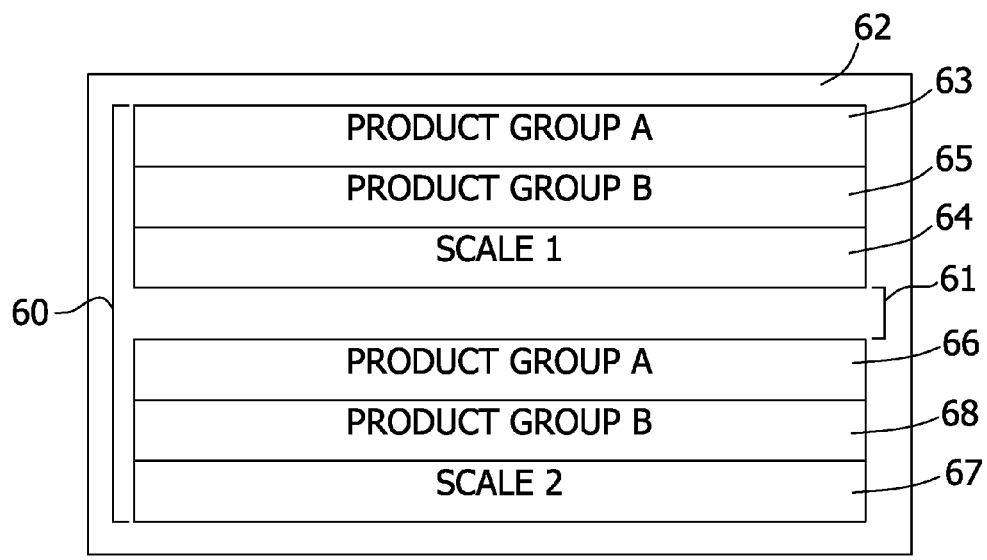
Figure 5C:
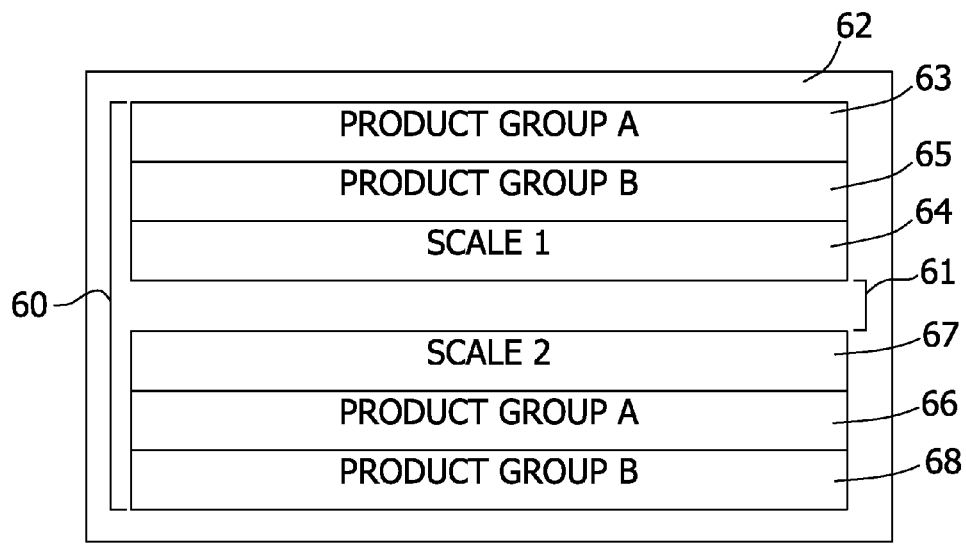
Figure 5D:
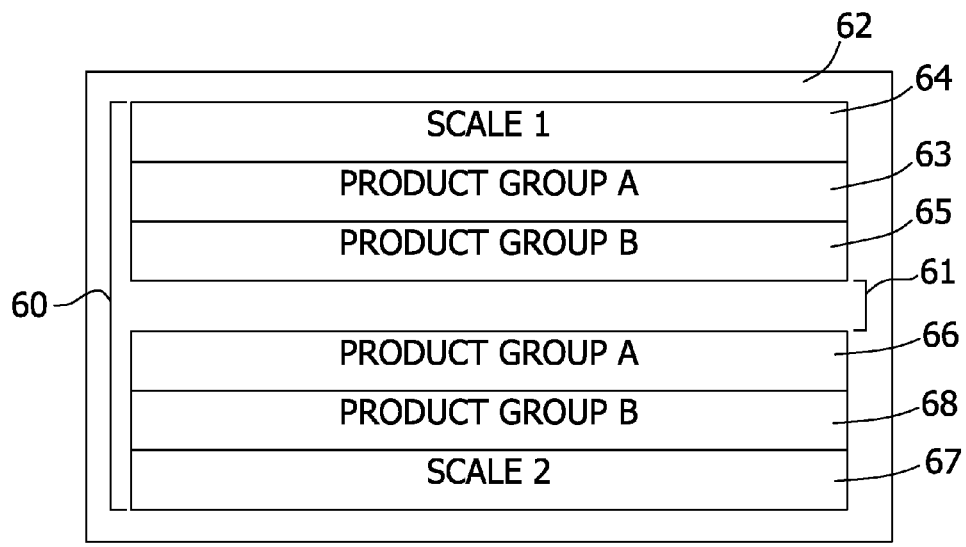

The products depicted in the first region 63 and the second region 65 are positioned within their respective regions so that the individual products line up with the value on the scale in the third region 64 that represents the product's particular characteristic (e.g., some feature, attribute, or benefit of the product), and the products depicted in the fourth region 66 and the fifth region 68 are positioned within their respective regions so that the individual products line up with the value on the scale in the sixth region 67. When using this configuration, it is typically advantageous to group the regions depicting the product groups to be compared with the region comprising the scale by which the comparison is made. Such grouping avoids confusion when the visual aid comprises multiple scales of reference. For example, referring again to FIG. 5A, the third region 64 comprising Scale 1 may be positioned so that it is adjacent to the two regions 63, 65 depicting the groups of products that are being compared using Scale 1. Alternately, as illustrated in FIGS. 5B, 5C, and 5D, the region 64 comprising Scale 1 may be positioned so that it is adjacent to only one of these regions 63, 65. A similar positioning may be used for the region 67 comprising Scale 2 and the two regions 66, 68 depicting the groups of products that are being compared using Scale 2.

In another embodiment, the visual aid may be used to compare one group of related products using two or more different scales of reference. For example, a group of related products may be evaluated according to different characteristics, using two or more scales of reference that each depict a different characteristic of the group of related products. Such a comparison is particularly useful when a consumer is interested in determining what product best satisfies a mixture of different characteristics.

Figure 6A:
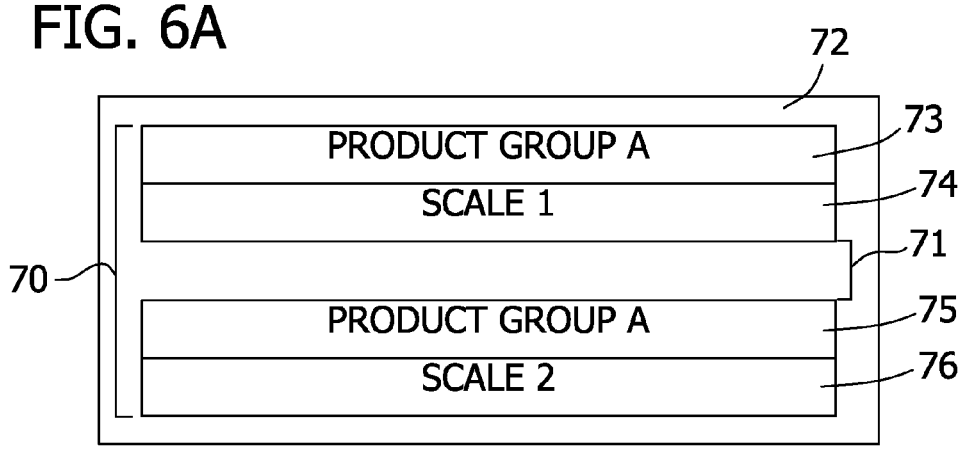
FIGS. 6A, 6B, and 6C illustrate various configurations of a transition aid of the present disclosure.
Figure 6B:
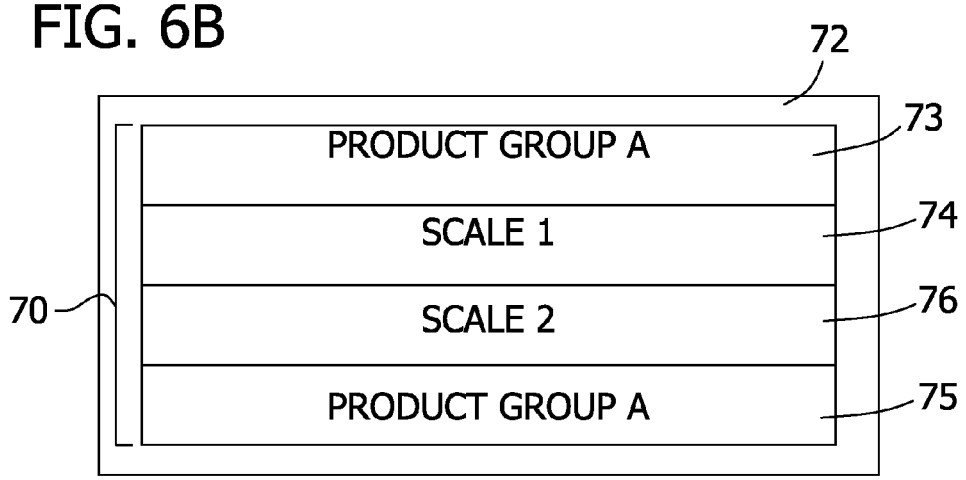
Figure 6C:
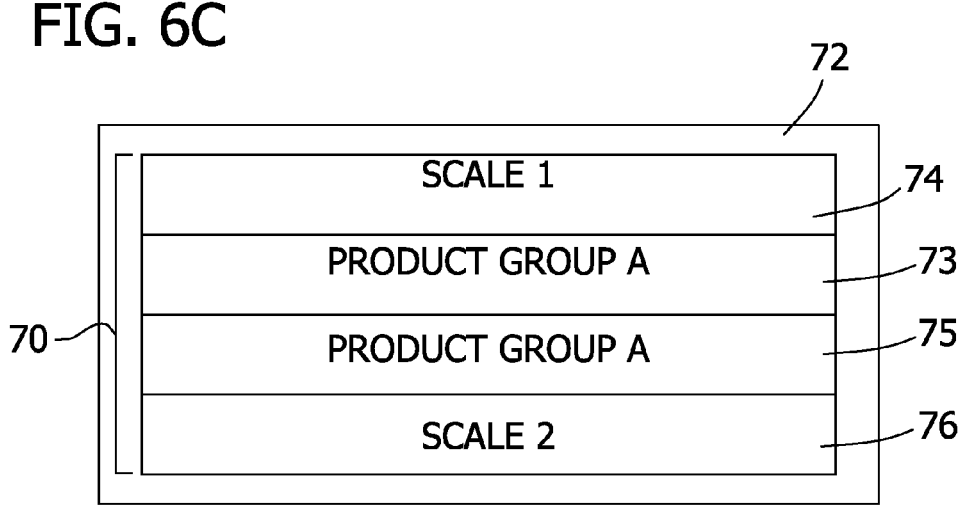

One example of this embodiment is illustrated in FIG. 6A. In FIG. 6A, the visual aid 70 comprises four different regions located on a medium 72. Two or more of the regions are optionally separated by a space 71 between regions. A first region 73 comprises a depiction of a group of related products (e.g., Product Group A), a second region 74 comprises a first scale of reference (e.g., Scale 1) that comprises a depiction of a first characteristic of Product Group A, a third region 75 comprises another depiction of Product Group A, and a fourth region 76 comprises a second scale of reference (e.g., Scale 2) that comprises a depiction of a second characteristic of Product Group A. Preferably, Scale 1 and Scale 2 each comprise a depiction of a different characteristic of the products in Product Group A. By providing two different scales of reference, the visual aid allows the same group of related products to be compared according to more than one characteristic. For example, Scale 1 may be used to depict the price of Product Group A, and Scale 2 may be used to depict a different characteristic of Product Group A, such as absorbency or another such attribute, feature, or benefit.

The products depicted in the first region 73 are positioned within the region so that the individual products line up with the value on the scale in the second region 74, and the products depicted in the third region 75 are positioned within the region so that the individual products line up with the value on the scale in the fourth region 76. When using this configuration, it is typically advantageous to group the regions so that the first region 73 is adjacent to the second region 74, and the third region 75 is adjacent to the fourth region 76. This grouping helps to avoid confusion when the visual aid comprises multiple scales of reference. Optionally, the visual aid may further comprise additional regions comprising still different scales of reference that are positioned on the visual aid adjacent to regions comprising a depiction of the products in Product Group A lined up along the scales.

In addition to the visual aid configurations specifically illustrated herein, one skilled in the art would understand that the visual aids may have other configurations, and may comprise multiple regions depicting additional groups of related products and additional scales of reference.

The transition aids described herein may be present on a variety of different media. For example, the visual aids may be present on any form of printed media including, for example, newspapers, pamphlets, magazines, displays, and various forms of advertisements, such as billboards, posters, banners, flyers, other forms of direct-mail or out-of-home media, and the like. The transition aid may also be present on an electronic medium, such as a television, a computer screen, personal data assistant, cellular telephone, an internet display, and the like.

In one particular embodiment, the transition aid may be present as part of an in-store display or shelf set located in the general proximity of an absorbent product depicted in the transition aid. In one example of this embodiment, the display may be located between two or more shelves of products, with one or more shelf having one group of related products depicted in the transition aid, and another shelf or shelves having another group of related products depicted in the transition aid. The scale of reference provided by the transition aid allows for easy comparison between the groups of related products. The in-store display may be some form of printed material, or optionally, may be an interactive display, as described below.

In a preferred embodiment, an absorbent article, an absorbent article wrapper, and/or a package of absorbent articles may comprise a transition aid. Absorbent articles may optionally be folded and/or individually packaged in various ways. For example, the absorbent articles may be folded and placed in an individual envelope or wrapper, or in other operative individual packaging. The wrapper may be formed from a separate piece of wrapper material using any methods known in the art. For example, the wrapper may be formed by sealing together various portions of a wrapper material in order to form an individual envelope or pouch that may encase the absorbent article. The wrapper generally comprises an interior and an exterior side, with the interior side facing the absorbent article and forming a hollow interior for receiving the absorbent article. The wrapper may be sealed by heat-sealing, by crimp sealing, and/or by using a suitable adhesive, among other means. Such methods of sealing are commonly known in the art. In certain embodiments, the wrapper may optionally comprise opening aids, such as grasping means in the form of flaps, fins, tear strips, or the like, which increase ease of opening of the package by improving accessibility of an end edge of the wrapper material. In this instance, the wrapper is generally opened by pulling on a free edge of the wrapper material, which breaks the sealing of the wrapper (e.g., breaks an adhesively sealed wrapper), thus allowing the absorbent article to be removed from the wrapper.

The wrapping layer can comprise any operative material. For example, the wrapping material can comprise a polymer film, a woven fabric, a nonwoven fabric, paper, cardboard, a composite laminate or the like, and combinations thereof.

An absorbent article may also be grouped together with several other absorbent articles to form a package of absorbent articles. The packages may comprise a plurality of the absorbent articles, preferably two or more individual absorbent articles, and more preferably comprise eight, ten, or twenty absorbent articles per package. The absorbent articles that are packaged together may be individually wrapped, as discussed above, or optionally may be packaged unwrapped. In one embodiment, the package of absorbent articles comprises a plurality of the same type of absorbent article (e.g., a package of napkins, a package of tampons, etc.). Alternately, the package of absorbent articles may comprise more than one type of absorbent article packaged together (e.g., a package comprising tampons, napkins, panty liners, and combinations thereof).

The package may comprise a soft or hard packaging material. Soft packaging includes flexible envelopes and packages made of sheet plastic and/or paper. Hard packaging includes generally less flexible packages made of plastic (e.g., tubs and buckets), metal or cardboard, and combinations thereof. Examples of suitable packaging materials include, for example, paper, cardboards, polymeric materials, coated paper, composite structures, or any other suitable packaging material. The package can have any operative configuration. For example, the package may comprise a bag, a carton, a container, a box, or the like, as well as combinations thereof. The various panels of the package can be flexible panels, rigid panels, semi-rigid panels, or the like, as well as combinations thereof. As discussed above with respect to wrappers, the package may also be formed by sealing together various portions of a packaging material (i.e., a packaging) in order to form a package encasing the absorbent articles. The packaging generally comprises an interior and an exterior side, with the interior side facing the absorbent articles and forming a hollow interior for receiving the absorbent articles. In certain embodiments, the package may comprise an opening mechanism, which provides access to the absorbent articles. Such opening mechanisms include, for example, a perforated section of packaging, a grasping means in the form of flaps, fins, tear strips, or the like, which increase ease of opening of the package by improving accessibility of an end edge of the package material, and combinations thereof.

The transition aid may be packaged with a plurality of absorbent articles and contained in the hollow interior of the packaging and/or may be wrapped with an individual absorbent article and contained in the hollow interior of the wrapper. Alternately or in addition, the transition aid may be on a removable release material, such as a removable label, peel strip, tear strip, or other removable layer that may be attached to the absorbent article, the wrapper, and/or the package. For example, the transition aid may be located on an exposed surface of a removable release material, which is arranged to face outwardly toward the consumer. Alternately, the transition aid may be positioned on an interior surface of the removable release material, such that it is exposed to the consumer only upon removal of the removable release material. In one embodiment, the transition aid may be positioned on a removable release material used to cover a garment adhesive used to adhere an absorbent article to the undergarments of a wearer.

In one particular embodiment, a transition aid is present on the exterior of a package of absorbent articles. In this instance, the transition aid may be created by marking the package so that the transition aid is visually perceptible and understandable to the consumer. The markings can be applied on the package by printing, embossing, die-cutting, application of a discrete label on which the transition aid is located or, in general, by any other physical change in the form or character of the package such as to make the markings visually noticeable and understandable to the consumer. Optionally, there may be cut lines and/or perforations around the transition aid located on the package, to enable a consumer to remove the transition aid from the package or wrapper.

In instances where the transition aid is found on an absorbent article, an absorbent article wrapper, and/or on a package of absorbent articles, the absorbent article will typically be one of the products depicted on the transition aid. The scale or scales of reference provided by the transition aid allows a consumer to compare a characteristic(s) of that particular absorbent article to other absorbent articles depicted on the transition aid. In certain embodiments, the depiction of the absorbent article may be highlighted or otherwise emphasized for easier identification of the absorbent article on the transition aid. Optionally, the transition aid may be removed from the absorbent article, wrapper, and/or package and taken with the consumer to the store to aid the consumer in the selection of a new absorbent product or in the transition to a new absorbent product.

The present disclosure also provides various methods for assisting a consumer in transitioning from a current absorbent product to a future absorbent product. Such methods are typically interactive, i.e., the consumer has input on the selection and/or formation of the transition aid that is provided to the consumer. In this manner, the consumer is provided with a transition aid specifically designed for his or her needs.

Generally, such methods involve receiving personal information from the consumer about at least one need of the consumer and providing the consumer with a transition aid, such as those described herein, that is customized for the consumer. More particularly, the method typically comprises receiving personal information from the consumer about at least one need of the consumer, receiving information from the consumer about an absorbent product currently used by the consumer, selecting a first group of related absorbent products that comprise the current absorbent product choice of the consumer, optionally selecting at least one additional group of related absorbent products, and providing the consumer with a transition aid.

The method may alternately or additionally comprise receiving information about the availability of products from a store, a retailer, or another institution that provides products to consumers. In this instance the at least one additional group of related absorbent products typically comprises products that are available from a particular store. In this manner, a consumer may receive a customized transition aid that allows the consumer to determine what absorbent products available at a particular store are most suitable for his or her needs.

The information received from the consumer typically relates to one or more need of the consumer. For example, if a consumer is transitioning to or from an incontinence product, the information provided by the consumer may be information about the situation the user of the incontinence product is experiencing. Such information includes, for example, information about the incontinent person's self-recognition of incontinence of urine (e.g., very low, somewhat low, almost normal, normal), the incontinent person's tendency for removal of a disposable absorbent article (e.g., not removed by oneself, removed by oneself when should not, removed from oneself when should), the incontinent person's ability to be active in daily living (e.g., bedridden, can lift the hip/lie at side, can sit, can stand, can walk slowly, can walk), the body form balance of an incontinent person (e.g., thinner at thighs and normal waist, big and/or fat, normal), the body set of the incontinent person (e.g., can not open legs, cannot bend leg, etc.), the contents of the leakage (e.g., urine only, feces only, urine and feces), when and/or how urine incontinence occurs (e.g., stringingly, within short period after desire of urination, when pressure applied to stomach), the discharging speed of urine (e.g., trickle, low speed, high speed), the discharging amount of urine into a disposable absorbent article (e.g., all, about half, some, a little, fundamentally all is into toilet, all is into toilet), the kind and/or type of disposable absorbent article used by the incontinent person, the changing frequency of the disposable absorbent articles used by the incontinent person within a specified time period, the discharged amount of urine per one disposable absorbent article by an incontinent person (e.g., fully wet, half wet, quarter or below wet), the position of leakage if any from a disposable absorbent article worn by an incontinent person (e.g., front-center, back-center, legs, sides), the frequency and/or amount of feces which are discharged by an incontinent person into a disposable absorbent article, and other such information.

If a consumer is transitioning to or from a diaper or a training pant, the information provided by the consumer may be information relating to the diaper or training pant user's stage of development or mobility, such as prelocomotive stage (e.g., newborns and other immobile infants with a level of activity of little more than head raising or rolling over), crawling stage (e.g., toddlers that can sit, scoot, roll, and/or crawl), exploring stage (e.g., toddlers who can stand, walk, begin to run), learning stage (e.g., toddlers capable of doing things by themselves such as dressing and developing coordination which enables them to walk and run without losing balance), and training stage (e.g., toddlers undergoing toilet training).

If a consumer is transitioning to or from a feminine hygiene product, the information provided by the user may include information relating to body size (e.g., petite, small, medium, large), flow intensity (including information about flow intensity indicators such as age, type of birth control used, number of pregnancies, consumer's self-perception of her flow intensity), period duration and volume, experienced soiling patterns (e.g., rarely soil ends/sides, occasionally soil ends/sides, often soil ends/sides, almost always soil ends/sides), panty size, hip size, clothing size in general, body mass index, other anthropometric information, panty style (e.g., "thong" style, "bikini" style, "hipster" style, "French cut" or "high cut," "briefs," etc.), preferred characteristics of the product, such as product absorbency, product thicknesses, product lengths, types of product features (e.g., wings/non-wings), and other such information.

Optionally, general information about the consumer may also be provided. The general information about the consumer includes, for example, the consumer's name, the consumer's ID number, the e-mail address and/or phone number of the consumer, the consumer's sex and age, information about prior purchases of the consumer, etc. Such information may be used to identify the consumer and, in certain instances, access information previously provided by the consumer.

In addition to information about the consumer's needs, the consumer may also provide information about the absorbent product currently being used by the consumer. Such information may include, for example, information about various characteristics of the current product such as the current product type (e.g., tampon, incontinence pad, panty liner, etc.), the current brand, the company that manufactures the product, price, and/or specific features, attributes, and benefits of the current product, as discussed herein.

The information is typically received from the consumer through an interactive means. For example, the consumer may input information into a user interface (e.g., speaking the information, selecting the appropriate information from a menu of items in a graphical user interface, typing in a code, product name, or other information, pressing a button specific to a certain piece of information, using an interactive menu-driven phone system, etc.). A user interface may include, for example, a mobile, cellular telephone; an electronic, personal data assistant; an electronic computer configured with an operative user-interface, such as a graphical user interface; a website; an electronic display; or the like. In one embodiment, an interactive computer can prompt a consumer to input several key pieces of information about his or her needs and current product choice.

In one embodiment, the information received from the consumer will be in response to questions. The consumer's response to these questions may then be used to formulate a customized transition aid for the consumer. These questions may be focused on gathering information about the consumer's needs, such as the information described above. Furthermore, these questions may be asked of the consumer in any suitable fashion, for example, via interactive site on the World Wide Web, an interactive in-store display or interactive computer, or through the use of an interactive menu-driven phone system.

In one embodiment, the transition aid provided to the consumer may, for example, be based on a profile, segment, and/or classification of consumers generally. That is, the entire group of consumers having similar needs may be separated into distinct categories for which suitable transition aids may be provided. These categories may be identified as profile, segment, and/or classification. This separation into profile, segment, and/or classification may be produced in any suitable fashion, including but not limited to, questions asked of consumers, such as questions about habits, traits, personality, and/or responses to visual situations and/or images of the consumers. The profile, segment, and/or classification into which a particular consumer belongs to may be similarly performed. Questions similar to those used in identifying the profile, segment, and/or classification may be used to generate the customized transition aid for the consumer depending on which profile, segment, and/or classification the consumer belongs to. These questions, for example, may be based on habits, traits, personality, and/or responses to visual situations and/or images of the consumers. Suitable types of questions include questions designed to gather psychographic information, demographic information, and physiological information about the consumer.

One skilled in the art will readily appreciate that numerous combinations of either individual questions or groups of questions may be asked in order to collect sufficient information to provide the basis for generating a transition aid for any particular consumer. The precise manner and wording chosen to collect this information from the consumer may vary depending on local custom, the comfort level consumers in a particular area may have in answering questions pertaining to their needs, and the shades of meaning associated with terms which may be used in different parts of the world to collect the information desired. It is to be further understood that the methods of the present disclosure are not to be limited to any one type of question asking methodology or philosophy.

In instances where information is received from a store about the availability of products, the information is typically received electronically. For example, the information may be received by accessing a database that contains information about product availability at a particular store or stores.

Once the information has been received from the consumer, a first group of related absorbent products may be selected. Typically, the first group of related products comprises the current product choice of the consumer. The first group of related products may be related to each other according to any of a variety of different product characteristics, such as those discussed herein. The first group of absorbent products and the particular characteristic or characteristics by which the products are related may be selected by the consumer (e.g., by the consumer inputting the choice into the user interface), or alternately, may be automatically generated based on the information received from the consumer about his or her needs and/or the current product choice.

Optionally, at least one additional group of related products may also be selected. In certain instances, this group or groups of related products may comprise the consumer's future product choice. The additional group or groups of related products may be related to each other according to any of a variety of different product characteristics, such as those discussed herein. Typically, the characteristic by which the products are related is either selected by the consumer (e.g., by the consumer inputting the choice into the user interface), or alternately, is automatically selected based on information received from the consumer about his or her needs. Likewise, the particular products in the additional group may be products selected by the consumer, or may be automatically determined based on the information received from the consumer. For example, if a consumer is interested in determining how his or her current product choice compares to another particular product or group of products, the consumer may select a first group of related products that comprises his or her current product choice and an additional group or groups of related products that comprise the product or products the consumer wishes to compare. In certain embodiments, the additional group or groups of related products may be selected based on the availability of the products at a particular store.

The consumer may then be provided with a transition aid. Typically, the transition aid is displayed on the user interface. In one embodiment, the transition aid comprises a first region comprising a depiction of the first group of related absorbent products, a second region comprising a depiction of at least one additional group of related absorbent products, and a third region comprising at least one scale of reference. The scale of reference comprises a depiction of a common characteristic of both the first group of related absorbent products and of the additional group or groups of related absorbent products. The characteristic depicted in the scale of reference may be chosen by the consumer, or alternately, may be automatically selected based on the information received from the consumer. Like discussed above, the depiction of each of the absorbent products in the first and the additional regions is positioned along the scale of reference so that the depiction of the product lines up in some manner with the corresponding markings on the scale of reference. It will be appreciated by those skilled in the art that the transition aid provided may have any of a variety of configurations depending on the products selected, the information received from the consumer, and/or the desired comparisons to be made. The consumer may then compare his or her current absorbent product to other absorbent products on the market using the transition aid provided.

In one embodiment, the method may optionally further comprise recommending a future absorbent product choice to the consumer. Typically, the recommended future absorbent product choice is among the products in the additional group or groups of related products depicted in the transition aid. The recommendation is generally based on the information received from the consumer about his or her needs.

Optionally, the consumer may be offered a choice of purchasing the recommended product. For example, the consumer may opt to have the recommended product delivered to the consumer by means of a delivery system, such as the United States Postal Service, FedEx, UPS, etc.

Having described the disclosure in detail, it will be apparent that modifications and variations are possible without departing from the scope of the disclosure defined in the appended claims.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description and shown in the accompanying drawings shall be interpreted as illustrative and not in a limiting sense.

What is claimed is:

1. A method for creating a package comprising a transition aid for transitioning a consumer from an absorbent product in a first product category to an absorbent product in a second product category, the method comprising:
    selecting a first absorbent product in the first product category;
    receiving, from the consumer, a selection of a common characteristic that each of the first absorbent product and a second absorbent product is to share;
    selecting, by a processor, the second absorbent product in a second product category, wherein the first absorbent product and the second absorbent product have the common characteristic; and
    creating a package for the first absorbent product, wherein the package comprises:
        a plurality of the first absorbent product;
        at least one sample of the second absorbent product; and
        a transition aid, the transition aid comprising a first region comprising a depiction of the first absorbent product, a second region comprising a depiction of the second absorbent product, and a third region comprising at least one scale of reference comprising a depiction n of the common characteristic of both the first absorbent product and the second absorbent product, wherein the depiction of each of the first absorbent product and the second absorbent product is positioned along the scale to indicate the common characteristics of each of the first absorbent product and the second absorbent product.

2. The method of claim 1, wherein selecting a first absorbent product in a first product category comprises receiving a selection of the first absorbent product in the first product category from the consumer.

3. The method of claim 1, further comprising receiving at least one feature designated by the consumer as being a desired feature the second absorbent product should include, and wherein the common characteristic of the first absorbent product and the second absorbent product includes the at least one desired feature.

4. The method of claim 3, wherein the common characteristic comprises one or more of the following: a feature, a benefit, an attribute, a brand, a company, and a manufacturer.

5. The method of claim 1, wherein the first absorbent product and the second absorbent product are one or more of the following: diapers, training pants, adult incontinence products, and feminine hygiene products.

6. The method of claim 1, further comprising enabling the consumer to purchase the created package.

7. A system for creating a package comprising a transition aid for transitioning a consumer from an absorbent product in a first product category to an absorbent product in a second product category, the system comprising:
    a computing device; and
    a processor programmed to:
    receive, from the consumer, a selection of a first absorbent product in the first product category;
    receive, from the consumer, a selection of a common characteristic that each of the first absorbent product and a second absorbent product is to share;
    select the second absorbent product in a second product category, wherein the first absorbent product and the second absorbent product have the common characteristic; and
    provide instructions to create a package for the first absorbent product, wherein the package comprises:
        a plurality of the first absorbent product;
        at least one sample of the second absorbent product; and
        a transition aid, the transition aid comprising a first region comprising a depiction of the first absorbent product, a second region comprising a depiction of the second absorbent product, and a third region comprising at least one scale of reference comprising a depiction of the common characteristic of both the first absorbent product and the second absorbent product, wherein the depiction of each of the first absorbent product and the second absorbent product is positioned along the scale to indicate the common characteristics of each of the first absorbent product and the second absorbent product.

8. The system of claim 7, wherein the processor is further programmed to receive at least one feature designated by the consumer as being a desired feature the second absorbent product should include, and wherein the common characteristic of the first absorbent product and the second absorbent product includes the at least one desired feature.

9. The system of claim 8, wherein the common characteristic comprises one or more of the following: a feature, a benefit, an attribute, a brand, a company, and a manufacturer.

10. The system of claim 7, wherein the first absorbent product and the second absorbent product are one or more of the following: diapers, training pants, adult incontinence products, and feminine hygiene products.

11. The system of claim 7, wherein the processor is further programmed to receive a purchase order from the consumer, the purchase order comprising a request to purchase one or more of the created package.

12. A package comprising:
a plurality of a first absorbent product from a first product category; and
a transition aid, the transition aid comprising a first region comprising a depiction of the first absorbent product, a second region comprising a depiction of a second absorbent product from a second product category wherein the first absorbent product and the second absorbent product have a common characteristic selected by a consumer, and a third region comprising at least one scale of reference comprising a depiction of the common characteristic of both the first absorbent product and the second absorbent product, wherein the depiction of each of the first absorbent product and the second absorbent product is positioned along the scale to indicate the common characteristics of each of the first absorbent product and the second absorbent product.

13. The package of claim 12, wherein the at least one scale depicts a range of values for the common characteristic of the first absorbent product and the second absorbent product.

14. The package of claim 12, further comprising a second scale of reference comprising a depiction of a second common characteristic of the first absorbent product and the second absorbent product.

15. The package of claim 12, wherein the common characteristic comprises one or more of the following: a feature, a benefit, an attribute, a brand, a company, and a manufacturer.

16. The package of claim 12, wherein the first absorbent product and the second absorbent product are one of the following: diapers, training pants, adult incontinence products, feminine hygiene products.

17. The package of claim 12, wherein the transition aid is one or more of the following: located on an exterior of the package, within a hollow interior of the package, wrapped within one or more of the plurality of the first absorbent product, and wrapped within the at least one sample of the second absorbent product.

18. The package of claim 17, wherein the transition aid may be located on a removable release material, and wherein the transition aid is further located on one or more of the following: an exposed surface of the removable release material, such that the transition aid is arranged to face outwardly toward the consumer; an interior surface of the removable release material, such that the transition aid is exposed to the consumer only upon removal of the removable release material; and a material used to cover a garment adhesive used to adhere one of the plurality of the first absorbent products or to the at least one sample of the second absorbent product of a wearer.

* * * * *